United States Patent [19]

Niemczyk

[11] 4,335,042
[45] Jun. 15, 1982

[54] PROCESS TO PRODUCE IMIDAZOBENZODIAZEPINE INTERMEDIATES

[75] Inventor: Henry J. Niemczyk, Wayne, N.J.

[73] Assignee: Hoffmann-La Roche Inc., Nutley, N.J.

[21] Appl. No.: 142,581

[22] Filed: Apr. 21, 1980

[51] Int. Cl.³ .................. C07D 243/16; C07D 401/04
[52] U.S. Cl. ........................... 260/239 BD; 260/244.4
[58] Field of Search ................................ 260/239 BD

[56] References Cited

U.S. PATENT DOCUMENTS 4,166,185  8/1979  Walser et al. ................. 260/239 BD
4,170,649 10/1979  Liepmann et al. ........... 260/239 BD

*Primary Examiner*—Alton D. Rollins
*Attorney, Agent, or Firm*—Jon S. Saxe; Bernard S. Leon; Frank P. Hoffman

[57] ABSTRACT

A process to produce a compound of the formula

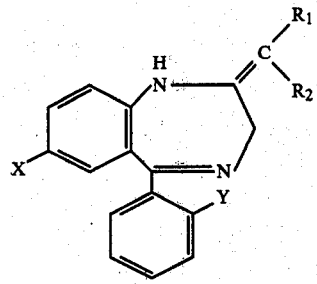

wherein $R_1$ and $R_2$ are selected from the group consisting of the groups $C_2H_5OOC-$, $CH_3OOC-$ and $N\equiv C-$, with the limitation that $R_1$ and $R_2$ cannot both be $N\equiv C-$, Y is hydrogen or halogen and X is selected from the group consisting of hydrogen halogen and nitro The compound is useful as an intermediate in the production of imidazobenzodiazepines, compounds having pharmacological activity.

3 Claims, No Drawings

PROCESS TO IMIDAZOBENZODIAZEPINE INTERMEDIATES

DESCRIPTION OF THE INVENTION

The present invention relates to a process to produce a compound of the formula

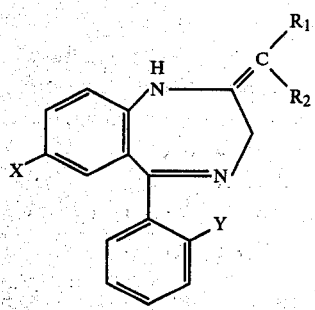

wherein $R_1$ and $R_2$ are selected from the group consisting of the groups $C_2H_5OOC-$, $CH_3OOC-$ and $N\equiv C-$, with the limitation that $R_1$ and $R_2$ cannot both be $N\equiv C-$, Y is hydrogen or halogen and X is selected from the group consisting of hydrogen, halogen and nitro The compound of formula I is useful as an intermediate in the production of imidazobenzodiazepines which are compounds having activity as sedatives, muscle relaxants, anticonvulsants and anxiolytic agents. A teaching of how to convert the compounds of formula I into imidazobenzodiazepines is found in U.S. patent application Ser. No. 904,951 which is incorporated herein by reference.

As used herein the term "halogen" shall mean chlorine, fluorine, bromine and iodine.

The present invention is a two step in situ process to the compounds of formula I which is set forth below:

lected from the group consisting of hydrogen, halogen and nitro.

The compound of formula I is formed by the reaction of an alkali metal hydride, e.g., sodium hydride and either diethylmalonate, ethylcyanoacetate or dimethylmalonate in an inert ether, such as, tetrahydrofuran or dioxane or other inert solvents, such as, dimethylformamide or methylene chloride in order to form the anion which is reacted with diethyl chlorophosphate to form the phosphonate Anion II. Thereafter in situ the compound of formula I is reacted with a benzodiazepin-2-one of formula III. The same solvents are utilized for both steps and the reaction temperature for both steps may range from about 0° C. to reflux temperature of the selected solvent with about room temperature as preferred.

The following examples are illustrative, but not limitative of this invention. All temperatures given are in degrees centigrade, unless indicated otherwise.

EXAMPLE 1

7-Chloro-5-(2-fluorophenyl)-2-diethoxymalonylidene-1,3-dihydro-2H-1,4-benzodiazepine Diethylmalonate (91 ml, 0.60 m) was added to THF (300 ml). The mixture was maintained at room temperature with a wet ice bath while sodium hydride (32 g of a 60% oil dispersion) was added over 1 hr. To the resulting suspension, diethyl chlorophosphate (29 ml) was added over 50 minutes. After a 30 minute agitation cycle, a THF solution of 7-chloro-5-(2-fluorophenyl)-1,3-dihydro-2H-1,4-benzodiazepin-2-one (28.85 g) was added dropwise over 20 minutes. The resulting solution was allowed to agitate for 2 hrs, after which the pH was adjusted to 5.0 to 5.5. Most of the THF was removed under vacuum (40° C./30 mm), and cold water (600 ml) was added, followed by hexane (100 ml). The resulting suspension was filtered and washed with water and hexane. After the solid was dried the end product was obtained.

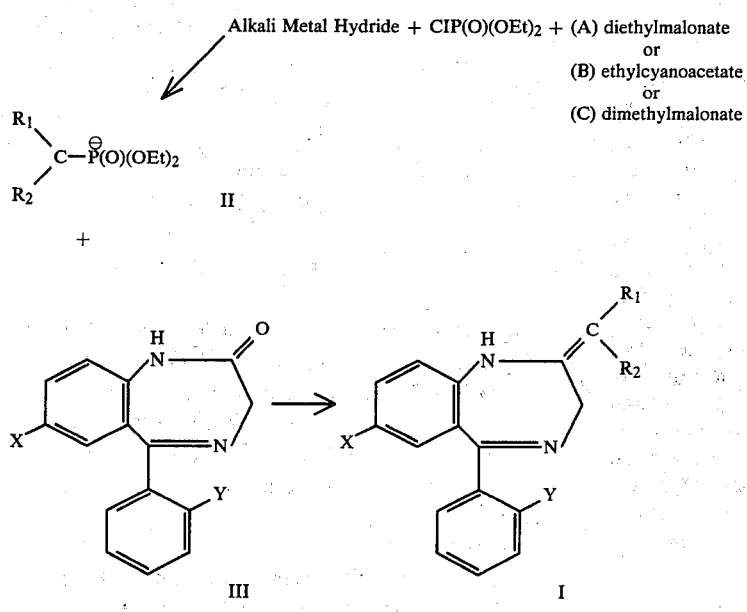

wherein $R_1$ and $R_2$ are selected from the group consisting of the groups $C_2H_5OOC-$, $CH_3OOC-$ and $N\equiv C-$ with the limitation that $R_1$ and $R_2$ cannot both be $N\equiv C-$, Y is hydrogen and halogen and X is se-

EXAMPLE 2

7-Chloro-1,3-dihydro-5-phenyl-2H-1,4-benzodiazepin-2-ylidenepropanedioic acid diethyl ester Diethylmalonate (45.55 ml) was added to tetrahydrofuran (200 ml). The mixture was maintained at room temperature while sodium hydride (16 g of a 60% oil dispersion) was added over 1 hr. To the resulting suspension, diethyl chlorophosphate (14.45 ml) was added dropwise over 50 minutes. After a 30 minute agitation cycle, a THF solution of 7-chloro-5-phenyl-1,3-dihydro-2H-1,4-benzodiazepin-2-one (13.54 g) was added dropwise over 20 minutes. The resulting solution was allowed to agitate for 1 hr. The pH was adjusted with acetic acid from 5.0 to 5.5, and the reaction solution was concentrated under vacuum (40° C./30 mm) to remove the THF. To the residue was added cold water (600 ml) and hexane (100 ml). The crystalline solid obtained was filtered and washed with water and hexane. After the solid was dried, the end product was obtained.

EXAMPLE 3

7-Bromo-1,3-dihydro-5-(2-pyridyl)-2H-1,4-benzodiazepin-2-ylidenepropanedioic acid diethyl ester Diethylmalonate (45.55 ml) was added to THF (200 ml). The mixture was maintained at room temperature while sodium hydride (16 g of a 60% oil dispersion) was added over 1 hr. To the resulting suspension, diethyl chlorophosphate (14.45 ml) was added dropwise over 50 minutes. After a 30 minute agitation cycle, a THF solution of 7-bromo-1,3-dihydro-5-(2-pyridyl)-2H-1,4-benzodiazepin-2-one (15.8 g) was added dropwise over 20 minutes. The resulting solution was allowed to agitate for 1 hr. The pH was adjusted from 5.0 to 5.5, and the reaction solution was vacuum concentrated (40° C./30 mm) to remove the THF. To the residue was added cold water (600 ml) and hexane (100 ml). The crystalline solid obtained was filtered and washed with cold water and hexane. After the solid was dried to constant weight, the end product was obtained.

EXAMPLE 4

7-Chloro-5-(2-chlorophenyl)-1,3-dihydro-2H-1,4-benzodiazepin-2-ylidenepropanedioic acid diethyl ester Diethylmalonate (45.55 ml) was added to THF (200 ml). The mixture was maintained at room temperature with a wet ice bath while sodium hydride (14 g of a 60% oil dispersion) was added portionwise over 1 hr. To the resulting suspension, diethyl chlorophosphate (14.45 ml) was added dropwise over 50 minutes. After a 30 minute agitation cycle, a THF solution of 7-chloro-5-(2-chlorophenyl)-1,3-dihydro-2H-1,4-benzodiazepin-2-one (15.25 g) was added dropwise over 20 minutes. The resulting solution was allowed to agitate for 1 hr. The pH was adjusted from 5.0 to 5.5, and the reaction solution was concentrated (40° C./30 mm) to remove the THF. To the residue was added cold water (600 ml) and hexane (100 ml). The crystalline solid obtained was filtered and washed with cold water and hexane. After the solid was dried to constant weight, the end product was obtained.

EXAMPLE 5

5-(2-Chlorophenyl)-1,3-dihydro-7-nitro-2H-1,4-benzodiazepin-2-ylidenepropanedioic acid diethyl ester Diethylmalonate (45.55 ml) was added to THF (200 ml). The mixture was maintained at room temperature with a wet ice bath while sodium hydride (16 g of a 60% oil dispersion) was added portionwise over 1 hr. To the resulting suspension, diethyl chlorophosphate (14.45 ml) was added dropwise over 50 minutes. After a 30 minute agitation cycle, a THF solution of 5-(2-chlorophenyl)-7-nitro-2H-1,4-benzodiazepin-2-one (15.8 g) was added dropwise over 20 minutes. The resulting solution was allowed to agitate for 1 hr. The pH was adjusted from 5.0 to 5.5, and the reaction was concentrated (40° C./30 mm) to remove the THF. To the residue was added cold water (600 ml) and hexane (100 ml). The crystalline solid obtained was filtered and washed with cold water and hexane. After the solid was dried to constant weight, the end product was obtained.

EXAMPLE 6

7-Chloro-5-(2-fluorophenyl)-1,3-dihydro-2H-1,4-benzodiazepin-2-ylidenecyano acetic acid ethyl ester Ethyl cyanoacetate (32.13 ml) was added to THF (200 ml) followed by a gradual addition of sodium hydride (16 g) over 1 hr. To the resulting suspension, was added diethyl chlorophosphate (14.45 ml). After agitating for 30 minutes, a THF solution of 7-chloro-5-(2-fluorophenyl)-1,3-dihydro-2H-1,4-benzodiazepin-2-one (14.43 g) was added dropwise over 1 hr. After a 1 hr agitation cycle, the solution was neutralized to pH 5 with acetic acid and quenched into water (500 ml) and hexane (300 ml). The resulting suspension of crystals was filtered and washed with water and hexane. After the crystals were dried to constant weight, the end product was obtained.

What is claimed is:

1. A process to produce a compound of the formula

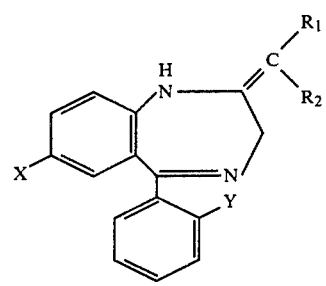

wherein $R_1$ and $R_2$ are selected from the group consisting of the groups $C_2H_5OOC-$, $CH_3OOC-$ and $N\equiv C-$ with the limitation that $R_1$ and $R_2$ cannot both be $N\equiv C-$, Y is hydrogen or halogen and X is selected from the group consisting of hydrogen, halogen and nitro which comprises (A) reacting an alkali metal hydride with a compound selected from the group consisting of diethylmalonate, ethylcyanoacetate and dimethylmalonate, followed by reaction with diethyl chlorophosphate and (B) reacting the product of (A) with a benzodiazepin-2-one of the formula

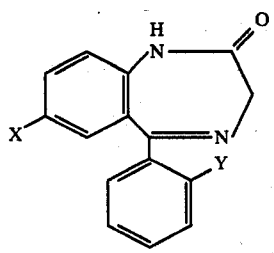

wherein X and Y are as above
to produce the final product.

2. The process of claim 1 wherein the alkali metal hydride is reacted with diethylmalonate.

3. The process of claim 2 wherein the alkali metal hydride is sodium hydride.

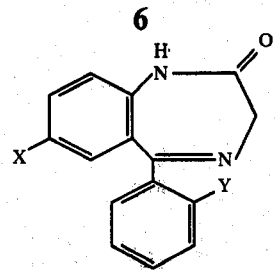

wherein X and Y are as above
to produce the final product.

2. The process of claim 1 wherein the alkali metal hydride is reacted with diethylmalonate.

3. The process of claim 2 wherein the alkali metal hydride is sodium hydride.